US010059658B2

(12) United States Patent
Bujnowski et al.

(10) Patent No.: US 10,059,658 B2
(45) Date of Patent: Aug. 28, 2018

(54) METHOD FOR PREPARATION OF 5-ALKYLSALICYLALDOXIMES AND APPLICATION THEREOF

(71) Applicant: Politechnika Warszawska, Warsaw (PL)

(72) Inventors: Krzysztof Bujnowski, Warsaw (PL); Ludwik Synoradzki, Warsaw (PL); Jerzy Wisialski, Warsaw (PL); Agnieszka Krolikowska, Warsaw (PL); Jacek Bordzilowski, Gdansk (PL); Marcin Koziorowski, Warsaw (PL); Roman Zadrozny, Warsaw (PL); Anna Jerzak, Warsaw (PL); Krzysztof Dzienis, Warsaw (PL)

(73) Assignee: POLITECHNIKA WARSZAWSKA, Warsaw (PL)

( * ) Notice: Subject to any disclaimer, the term of this patent is extended or adjusted under 35 U.S.C. 154(b) by 0 days.

(21) Appl. No.: 15/694,032

(22) Filed: Sep. 1, 2017

(65) Prior Publication Data

US 2017/0362168 A1 Dec. 21, 2017

Related U.S. Application Data

(63) Continuation of application No. PCT/PL2016/000021, filed on Mar. 1, 2016.

(30) Foreign Application Priority Data

Mar. 2, 2015 (PL) .......................... 411433

(51) Int. Cl.
*C07C 249/04* (2006.01)
*C07C 249/08* (2006.01)
*C09D 5/08* (2006.01)
*C23F 11/14* (2006.01)

(52) U.S. Cl.
CPC .......... *C07C 249/04* (2013.01); *C07C 249/08* (2013.01); *C09D 5/086* (2013.01); *C23F 11/147* (2013.01)

(58) Field of Classification Search
None
See application file for complete search history.

(56) References Cited

U.S. PATENT DOCUMENTS

| 4,324,922 A | 4/1982 | Smith | |
| 6,673,969 B2 * | 1/2004 | Seidl | C07C 249/08 |
| | | | 423/112 |
| 2002/0058700 A1 * | 5/2002 | Jensen | C07C 251/48 |
| | | | 514/524 |

FOREIGN PATENT DOCUMENTS

| CN | 104356025 A | 2/2015 |
| EP | 0125025 A2 | 11/1984 |
| EP | 0178850 B1 | 4/1986 |
| EP | 0584988 A1 | 3/1994 |
| GB | 1310808 A | 3/1973 |
| PL | 117888 B1 | 1/1983 |

OTHER PUBLICATIONS

Stepniak ("5-Hydroxy-5-alkylbenzaldehydes and their oximes" Polish Journal of Chemistry, vol. 54, 1980, p. 1567-1571).*
Stepniak-Biniakiewicz, "2-Hydroxy-5-Alkylbenzaldehydes and their Oximes", Polish Journal of Chemistry, pp. 1567-1571, vol. 54, 1980.
Stepniak-Biniakiewicz et al., "Preparation of 2-hydroxy-5-nonylbenzoic aldehyde oxime", Institute of Chemical Technology, Poznań University of Technology, pp. 11-12, vol. 61,1982.
Vogel, "Vogel's Textbook of Practical Organic Chemistry", pp. 1046-1049, 5th Edition, Longman Group UK Limited, 1989.
Birch, "The Evaluation of the New Copper Extractant P-1", Proceedings of the International Solvent Extraction Conference, ISEC 74, Lyon, pp. 2837-2870, Sep. 1974.
Thomson Scientific, "Synthesis of 5-nonylsalicylaldoxime", Feb. 18, 2015, English abstract for CN 104356025.
International Search Report, dated Jun. 1, 2016, for corresponding International Application No. PCT/PL2016/000021.

* cited by examiner

*Primary Examiner* — Jafar Parsa
*Assistant Examiner* — Amy C Bonaparte
(74) *Attorney, Agent, or Firm* — Myers Wolin, LLC

(57) ABSTRACT

Method for preparation of 5-alkylsalicylaldoximes with formula 1, where R is a C6-C16 alkyl group, consisting in that into a water-alcohol solvent system, p-alkylphenol, sodium hydroxide, chloroform and hydroxylamine are introduced, while in relation to the alkylphenol used, sodium hydroxide and chloroform are used in amounts from the stoichiometric amount to a 100% excess, and hydroxylamine is used in amounts from the stoichiometric amount to a 60% excess, and the reaction is carried out at a temperature of 60-75° C. for 1.5-4 h, and then, at a temperature of 20-30° C., the post-reaction mixture is acidified till the pH of the aqueous phase <7.0 is obtained, and next, an alcohol-water azeotrope is distilled off with an admixture of unreacted chloroform, the residue is mixed with a neutral C5-C10 hydrocarbon solvent, the layers are separated, and the solvent is distilled off from the organic phase.

8 Claims, No Drawings

METHOD FOR PREPARATION OF 5-ALKYLSALICYLALDOXIMES AND APPLICATION THEREOF

CROSS-REFERENCE TO RELATED APPLICATIONS

This is a continuation application of International Application PCT/PL2016/000021, filed Mar. 1, 2016, which claims priority to Polish application P.411433, filed Mar. 2, 2015, the contents of each of which are incorporated herein by reference.

FIELD

The invention relates to a method for preparation of 5-alkylsalicylaldoximes (5-alkyl-2-hydroxy-benzaldoximes) and an application of the reaction product as an anticorrosive

BACKGROUND 5-alkylsalicylaldoximes form stable complexes with iron, insoluble in water, thus effectively inhibiting the process of metal corrosion and rendering its surface hydrophobic. For example, Patent Description No. EP0178850 discloses an anticorrosive preparation, containing an aldoxime with two oxime groups in an onto position towards the hydroxyl group as an active substance. Oximes may be used for direct application to the metal surface, as well as in the form of a solution in a proper organic solvent or in the form of an aqueous emulsion. As the solvent in the preparation, alcohols, ethers, ketones and aromatic and aliphatic hydrocarbons may be used, e.g. ethanol, isopropanol, toluene, xylene, chloroform or 1,1,1-trichloroethane. Considering the commonness of corrosion, it is important that the preparations used for preventing this phenomenon are simple to obtain and inexpensive.

Known methods for preparation of aldoximes consist in a reaction of a proper aldehyde with hydroxylamine. The oldest of the known methods consists in adding an aqueous or methanol [1] [D. Stępniak-Biniakiewicz, *Pol. J. Chem.*, 54, 1567-1571, 1980] solution of hydroxylamine hydrochloride [2] [D. Stępniak-Biniakiewicz, A. Łukowski, *Przem. Chem.*, 61, 446-448, 1982], [3] [G. V. Jeffrey, *Soc. Chem. Ind. London*, 3, 2837-71, 1974], [4] [PL117888], [5] [A. I. Vogel, *Textbook of Practical Organic Chemistry/Preparatyka Organiczna, pp. 692-693, Warszawa, Wydawnictwo Naukowo-Techniczne,* 1984] or hydroxylamine sulfate [6] [Toagosei Chemical Industry CO. LTD, UK1310808, 1973] to a concentrated solution of the aldehyde in an alcohol, e.g. methanol [2] or ethanol, predominantly at the boiling temperature of the reaction mixture [5], adjusting the pH in the range of 5-8. Alternatively, the synthesis was also carried out without any addition of organic solvent, introducing the aldehyde directly into a prepared hydroxylamine solution, at a temperature of 30-50° C., with an addition of a hydroxylamine stabiliser, e.g. $Sn(OH)_2$ [6]. When the synthesis was completed and optionally the alcohol distilled off from the post-reaction mixture, the product was extracted with a neutral organic solvent non-miscible with water, e.g. diethyl ether [1], [5], or benzene or its derivatives [6]. The extract was washed with hydrochloric or sulfuric(VI) acid, then with water, until a neutral reaction was obtained. Next, the solvent was distilled off, and the product crystallised, if possible, from hexane, a hexane-benzene mixture [1] or chloroform-light gasoline mixture [5].

In order to produce the corresponding 5-alkylsalicylaldoximes, in general their producers must have a technique for preparation of the initial aldehydes at their disposal. In most cases, pure 5-alkylsalicylaldehydes are expensive or not readily available commercially—typically, they are not commercial products (apart from laboratory reagents).

One of the main methods for synthesis of 5-alkylsalicylaldehydes is the Reimer-Tiemann reaction, most often using sodium hydroxide, alkylphenol and chloroform as reagents and a water-methanol mixture as a solvent. According to standard procedure, a solution of the corresponding phenol in methanol is introduced into an aqueous NaOH solution or suspension, and then chloroform is added slowly under reflux, at the boiling temperature of methanol [1]. Alternatively, the corresponding phenol and the entire chloroform batch are introduced into the aqueous NaOH solution or suspension, and the reaction is carried out under pressure, at a temperature of 80-88° C. [7] [W. E. Smith, The Dow Chemical Company, U.S. Pat. No. 4,324,922, 1982]. In both variants, when the reaction is completed, the entire system is cooled to room temperature, unreacted NaOH and NaCl formed in the reaction are dissolved in water, and the post-reaction mixture is then acidified with sulfuric(VI) or hydrochloric acid, obtaining two layers: an aqueous phase and an organic phase. The separated organic phase is washed with water, and the aldehyde formed, depending on the applied phenol, is purified by fractional distillation under vacuum or crystallisation, e.g. from hexane [1]. In the second stage, the so-obtained aldehyde is subjected to a condensation reaction with hydroxylamine in order to obtain 5-alkylsalicylaldoxime, using the method described above.

The two-stage synthesis described above has the disadvantage of a relatively low yield of the first stage, or preparation of 5-alkylsalicylaldehyde—usually this does not exceed 35% in relation to the alkylphenol. The low yields and low conversion degree of alkylphenols are undoubtedly caused by an inhibition of the course of synthesis after reaching an equilibrium between the substrates and the products by the reaction system. It is easy to calculate that even if the yield of condensation of the so-produced aldehyde with hydroxylamine was close to 100%, the final yield of the oxime synthesis in the two-staged process: alkylphenol→aldehyde→oxime (being a product of yields of the individual stages) would not exceed 35%, and actually it could be even lower. Moreover, synthesis of aldehydes using this method leads to formation of many by-products, including polycondensation products [4]. Also, the necessity to isolate and purify the starting aldehyde is a significant inconvenience.

In 1994, a method for preparation of oximes by a reaction of magnesium salts of proper 5-alkylsalicylaldehydes with hydroxylamine, directly in the mixture after the synthesis of these salts, eliminating laborious isolation and purification of the aldehyde was disclosed [8] [D. Levin, Zeneca Limited, EP0584988A1, 1994]. At first, a salt of a proper p-alkylphenol with magnesium is prepared. To its mixture in toluene, paraform(aldehyde) is added portion-wise, and simultaneously, the methanol forming as a by-product in the reaction of these substrates is distilled off in the form of an azeotrope with toluene, achieving formylation of the onto position of the initial p-alkylphenol salt, and formation of a magnesium salt of the corresponding 5-alkylsalicylaldehyde, suspended or dissolved in toluene. Directly after formylation, at a temperature of 40-45° C., an aqueous hydroxylamine (or hydroxylamine sulfate(VI)) solution is introduced to the post-reaction mixture in order to obtain a oxime magnesium salt. In the end, the mixture is acidified with diluted sulfuric(VI) acid, and toluene is distilled off from the organic phase isolated and washed with water, yielding a raw product—the corresponding 5-alkylsalicylaldoxime, which is optionally purified by fractional distillation under vacuum or crystallisation. The method allows for obtaining the desired 5-alkylsalicylaldoximes from the starting alkylphenols in a "one pot" system with high yields, but the entire process is time-consuming and costly.

SUMMARY

The goal of the invention is to propose a method allowing for solving of the aforementioned problems.

DETAILED DESCRIPTION

Method for preparation of 5-alkylsalicylaldoximes with formula 1,

Formula 1

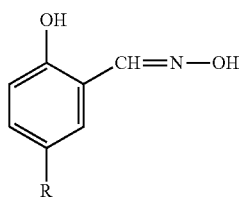

where R is a C6-C16 alkyl group, consisting in that into a water-alcohol solvent system, p-alkylphenol, sodium hydroxide, chloroform and hydroxylamine are introduced, while in relation to the alkylphenol used, sodium hydroxide and chloroform are used in amounts from the stoichiometric amount (i.e. 4 moles of sodium hydroxide/mole of alkylphenol, 1 mole of chloroform/mole of alkylphenol) to a 100% excess, preferably in a 50-100% excess, and hydroxylamine is used in amounts from the stoichiometric amount (i.e. 1 mole hydroxylamine/mole of alkylphenol) to a 60% excess, and the reaction is carried out at a temperature of 60-75° C., preferably at 63-71° C., for 1.5-4 h, and then, at a temperature of 20-30° C., the post-reaction mixture is acidified till the pH of the aqueous phase <7.0 is obtained, and next, an alcohol-water azeotrope is distilled off with an admixture of unreacted chloroform, the residue is mixed with a neutral C5-C10 hydrocarbon solvent, the layers are separated, and the solvent is distilled off from the organic phase.

Hydroxylamine is introduced in the form of an aqueous solution, preferably approx. 50%; optionally, it may be generated in the reaction system, in a reaction of hydroxylamine sulfate(VI) or hydrochloride with concentrated) solution of sodium hydroxide (introduced into the reaction system in an amount of 2 moles of NaOH/mole of hydroxylamine sulfate(VI) or 1 mole of lye/mole of hydroxylamine hydrochloride).

Preferably, the reaction is carried out in a water-alcohol solvent mixture with a mass ratio of 2:1 to 3:1. As the alcohol, preferably C2-C4 is used, preferably isopropanol. As the saturated hydrocarbon, preferably hexane, mixtures of C5-C10 liquid aliphatic hydrocarbons or toluene are used.

The invention also includes the application of the product obtained by the method according to the invention as a corrosion inhibitor, also enhancing the plasticity and adhesion of paint coatings. A raw oxime in a solvent, in concentrations up to 30%, may be used, after removal of mineral impurities, for coating of the metal surface, without additional purification. As the solvent, lower C2-C4 alcohols, ethers, ketones and aromatic and aliphatic hydrocarbons are used, e.g. ethanol, isopropanol, toluene, xylene, chloroform, hexane or 1,1,1-trichloroethane; optionally—mixtures of these solvents, for impregnation of steel surfaces before application of coating anticorrosive systems.

The method for preparation of 5-alkylsalicylaldoximes according to the invention is a one-stage process. A sodium salt of a proper 5-alkylsalicylaldehyde, forming in a reaction of the Reimer-Tiemann type, is condensed in statu nascendi in a water-alcohol medium with hydroxylamine, introduced in the form of an aqueous solution, optionally generated in the reaction system in a reaction of hydroxylamine sulfate (VI)/hydrochloride with soda lye, yielding an oxime sodium salt with a phenolate character, and the latter transforms itself into the corresponding oxime after acidification of the post-reaction mixture (Scheme 1). The content of oximes in the product usually amounts to 60-75%, and the formation yield, calculated per pure product—50-85%.

Scheme 1

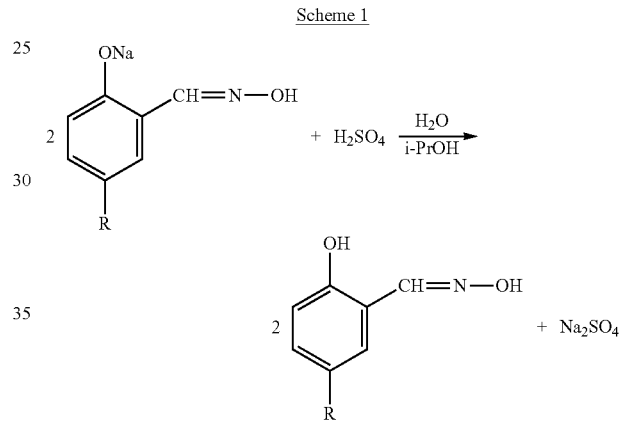

Such an immediate transformation of a salt of the forming aldehyde into an oxime salt has turned out to be possible using the procedure applied and simultaneously and unexpectedly yields a number of positive effects: it limits side reactions having characteristics of aldehyde condensation or polymerisation, accelerates the aldehyde syntheses, increases the degree of conversion of the starting alkylphenol. As a result, the entire process of oxime synthesis occurs rapidly, with a satisfactory selectivity and yield. The reaction product is a finished corrosion inhibitor, and there is no need for its separation from the reaction mixture.

The layer forming after application of a solution of the product obtained according to the invention to the metal surface provides the good adhesion of typical lacquer coatings to a corroded steel substrate, after removal of loose rust, as well as to chalked coatings after a wipe with a steel brush. Application of the product allows for elimination of costly, typically technically difficult and environmentally harmful procedures of thorough cleaning of steel surfaces, e.g. sandblasting, grinding, chemical etching, which are required when using most paints.

EXAMPLES

The method for preparation and application of oximes according to the invention is illustrated through the following examples.

Example 1. Preparation of 2-hydroxy-5-nonyl-benzaldoxime

In a reaction flask having a capacity of 0.25 l, 0.85 mole (34.0 g) of sodium hydroxide was dissolved in 54.0 g of water while mixing and cooling. Then, at a temperature of approx. 40° C., 0.1 mole (22.0 g) of p-nonylphenol ($C_{15}H_{24}O$) in 23.0 g of isopropanol was introduced into the flask. Simultaneously, a solution of 0.075 mole (12.5 g) of hydroxylamine sulfate(VI) (SHA) in 12.5 g of water at 60° C. was prepared. To the content of a reaction flask heated to 65° C., with vigorous stirring, 0.175 mole (20.8 g) of chloroform was added dropwise over 0.5 h, and at the same time—the prepared SHA solution was added, while maintaining a temperature within a range of 65-68° C. (the reaction is exothermic). After dropwise-adding these reagents, stirring of the reaction continued for approx. 1.5 h at the above temperature. The progress of the reaction was controlled chromatographically, by TLC (chloroform/hexane 4:1), observing a decay of the starting alkylphenol spot (total reaction time: approx. 2 h). The post-reaction mixture was then cooled to room temperature, and next, while mixing and cooling, 35% sulfuric(VI) acid was added portion-wise to the pH of the aqueous phase <7.0. At 80-95° C., an azeotrope of isopropanol with water with an admixture of unreacted chloroform was distilled off from the flask.

The post-distillation residue was cooled to a temperature of approx. 35° C. and then mixed for 0.25 h together with 30 g (approx. 44.0 ml) of hexane. After the separation of phases, the upper (organic) phase was washed with water. Hexane was distilled off from the organic solution. The residue after distillation is constituted by the raw product—2-hydroxy-5-nonyl-benzaldoxime (m=26.5 g) in the form of an oily olive-brown viscous liquid.

Based on the nitrogen content, determined by elemental analysis, the approximate amount of the main component—oxime—was calculated as equal to 64.2%. The yield in relation to the starting p-nonylphenol: 64.8%.

Example 2. Preparation of 2-hydroxy-5-nonyl-benzaldoxime

The procedure was as in Example 1, while the following reagents were used: 0.7 mole (28.0 g) of sodium hydroxide in 45.0 g of water, 0.1 mole (22.0 g) of p-nonylphenol ($C_{15}H_{24}O$) in 23.0 g of isopropanol, and 0.15 mole (4.95 g) of hydroxylamine in the form of a 50% aqueous solution at room temperature, as well as 0.175 mole (20.8 g) of chloroform. Consumption of sulfuric(VI) acid and hexane—similarly as in Example 1.

31.7 g of raw product—2-hydroxy-5-nonyl-benzaldoxime—was obtained, with the approximate content of the main component—oxime—equal to 68.9%. The yield in relation to the starting p-nonylphenol: 82.9%.

Example 3. Preparation of 2-hydroxy-5-dodecyl-benzaldoxime

The procedure was as in Example 2, while the following reagents were used: 0.7 mole (28.0 g) of sodium hydroxide in 45.0 g of demineralised water, 0.1 mole (26.3 g) of p-dodecylphenol ($C_{18}H_{30}O$), and 0.15 mole (4.95 g) of hydroxylamine in the form of a 50% aqueous solution at room temperature, as well as 0.175 mole (20.8 g) of chloroform. Total reaction time: 2.5 h. Consumption of sulfuric (VI) acid and hexane—similarly as in Example 1.

31.1 g of raw product—2-hydroxy-5-dodecyl-benzaldoxime—in the form of an oily olive-brown viscous liquid was obtained, with the approximate content of the main component—oxime—equal to 62.5%. The yield in relation to the starting p-dodecylphenol: 63.6%.

Example 4

Onto the surface of 6 steel plates, cleaned to a degree of St3 according to the PN-EN ISO 8501 standard (cleaning with brush; approx. 50% of the surface with rust remaining), preparation A was applied—raw oxime, prepared acc. to Example 1, diluted with isopropanol (approx. 10% solution), obtaining, after 4 h drying at room temperature, a layer containing approx. 5.5 g of raw oxime/m of the steel surface. A coating system was then applied, consisting of an epoxide prime coat with a thickness of 50 μm, an interlayer epoxide coat with a thickness of 100 μm and a polyurethane top coat with a thickness of 60 μm. The same painting system was applied onto the next 6 steel plates, prepared in the same way but without preparation A. After seasoning of the coats, a cross-cut with an intersection angle of 30° was made in the centre of the plate, on 3 plates of each series.

All the plates were placed in a salt spray chamber and tested according to the ISO 9227 standard, observing damages in the coats (spray with a 3% solution of sodium chloride at a temperature of 30±2° C.). In Tables 1 and 2, damages of the coats after a 1 440 h test in the salt spray chamber can be seen, evaluated according to the PN-EN ISO 4628 standard (I—plates without preparation A; II—plates with preparation A; X—plates with the cross-cut).

TABLE 1

Results of the tests in a salt spray chamber for plates without preparation A

| Sample | Time [h] | Damage type | Blisters | Rusting | Cracking | Flaking | Notes |
|---|---|---|---|---|---|---|---|
| Is-1 | 1440 | — | none | Ri1 | none | none | — |
| Is-2 | | — | none | Ri1 | none | none | — |
| Is-3 | | — | none | Ri1 | none | none | — |
| | | Pertains to the entire plate | | Area around the crack (to 8 mm) | | | |
| IsX-1 | 1440 | uniform | 1(S2) | Ri1 | 0(S0) | 0(S0) | |
| IsX-2 | | uniform | 1(S1) | Ri1 | 0(S0) | 0(S0) | |
| IsX-3 | | uniform | 1(S2) | Ri1 | 0(S0) | 0(S0) | |

TABLE 2

Results of the tests in a salt spray chamber for plates with preparation A

| Sample | Time [h] | Damage type | Blisters | Rusting | Cracking | Flaking | Notes |
|---|---|---|---|---|---|---|---|
| Is-1 | 1440 | — | none | Ri0 | none | none | — |
| Is-2 | | — | none | Ri0 | none | none | — |
| Is-3 | | — | none | Ri0 | none | none | — |
| | | Pertains to the entire plate | | Area around the crack (to 8 mm) | | | |
| IsX-1 | 1440 | uniform | 0(S0) | Ri0 | 0(S0) | 0(S0) | |
| IsX-2 | | uniform | 0(S0) | Ri0 | 0(S0) | 0(S0) | |
| IsX-3 | | uniform | 0(S0) | Ri0 | 0(S0) | 0(S0) | |

Where:

Ri1—rusting degree denoting rust on 0.05% of the surface. Rusting degrees are reported as increasing from Ri0 to Ri5.

Blistering, cracking and flaking are defined by their densities and sizes (the value in brackets) on a scale from 0 to 5 (0—the lowest density and the smallest size). As one can see, there is slight corrosion of the uncut samples and blistering near the cut on the plates without preparation A and corrosion on the plates with the cut. On both types of plates with preparation A, no damages occurred.

Example 5

Onto the surface of 3 plates of 5215 steel (formerly St3), cleaned to a degree of St3 according to the PN-EN ISO 8501 standard (cleaning with brush; approx. 50% of the surface with rust remaining), preparation A was applied—raw oxime, prepared acc. to Example 1, diluted with isopropanol (10% solution), obtaining, after 4 h drying at room temperature, a layer containing approx. 5.5 g of raw oxime/m of the steel surface. A coating system was then applied, consisting of an epoxide prime coat with a thickness of 50 μm and an interlayer epoxide coat with a thickness of 100 μm. The same painting system was applied onto the next 3 steel plates, prepared in the same way but without preparation A. After seasoning of the coats, studies by an impedance spectroscopy and coating adhesion test by the pull-off method according to the ISO 16276 standard were carried out. The plates were places in a humidity chamber, and a test of corrosion resistance according to the ISO standard was carried out for 1 440 h. After removal of the plates from the chamber, their appearance was evaluated, and the impedance spectroscopy test was repeated. The value of the logarithm of the impedance module at a frequency of 0.1 Hz shows the barrier properties of the coatings. Values exceeding 6 prove the presence of barrier properties. The higher the value, the better the barrier properties. No damage visible with the naked eye was found on any of the tested plates. For the impedance spectra in the Body system, the following values of the logarithm of the impedance module at a frequency of 0.1 Hz were found:

before the humidity chamber tests: 8-10 for all plates
after the humidity chamber tests: 8-10 for plates with preparation A;
7-10 for plates without preparation A.

The values of coating adhesion measured by the pull-off method amounted to: before the humidity chamber tests: 7-9 MPa for all plates; after the humidity chamber tests: 7-9 MPa for plates with preparation A and 4-5 MPa for plates without preparation A.

The obtained results prove better barrier properties of systems with preparation A after exposures in the humidity chamber, as well as their better adhesion after the same exposures.

What is claimed is:

1. A method for the preparation of 5-alkylsalicylaldoximes of formula 1,

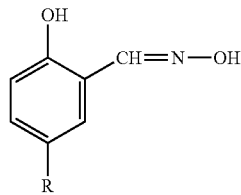

Formula 1 wherein R is a $C_6$-$C_{16}$ alkyl group, using the Reimer-Tiemann reaction, wherein into a water-alcohol solvent system, p-alkylphenol, sodium hydroxide, chloroform and hydroxylamine are introduced, while in relation to the alkylphenol used, sodium hydroxide and chloroform are used in amounts from the stoichiometric amount to a 100% excess, and hydroxylamine is used in amounts from the stoichiometric amount to a 60% excess, and the reaction is carried out at a temperature of 60-75° C. for 1.5-4 h, and then, at a temperature of 20-30° C., the post-reaction mixture is acidified until the pH of the aqueous phase <7.0 is obtained, and next, an alcohol-water azeotrope is distilled off with an admixture of unreacted chloroform, the residue is mixed with a neutral $C_5$-$C_{10}$ hydrocarbon solvent, the layers are separated, and the solvent is distilled off from the organic phase.

2. The method according to claim 1, wherein the hydroxylamine is introduced in the form of an aqueous solution.

3. The method according to claim 1, wherein the hydroxylamine is generated in the reaction system in a reaction with hydroxylamine sulfate (VI) or hydrochloride with soda lye.

4. The method according to claim 1, wherein the reaction is carried out in a water-alcohol solvent mixture with a mass ratio of 2:1 to 3:1.

5. The method according to claim 1, wherein in the solvent system a $C_2$-$C_4$ alcohol is used.

6. The method according to claim 1, wherein the neutral hydrocarbon solvent is hexane, mixtures of $C_5$-$C_{10}$ liquid aliphatic hydrocarbons, or toluene.

7. The method according to claim 2, wherein the concentration of the hydroxylamine in the aqueous solution is approx. 50%.

8. The method according to claim 5, wherein the $C_2$-$C_4$ alcohol is isopropanol.

* * * * *